US010281431B2

(12) United States Patent
Zhang et al.

(10) Patent No.: US 10,281,431 B2
(45) Date of Patent: May 7, 2019

(54) DARKROOM TYPE SECURITY INSPECTION APPARATUS AND METHOD (71) Applicant: Nuctech Company Limited, Haidian District, Beijing (CN)

(72) Inventors: Qingjun Zhang, Beijing (CN); Yuanjing Li, Beijing (CN); Zhiqiang Chen, Beijing (CN); Weiping Zhu, Beijing (CN); Ziran Zhao, Beijing (CN); Qiufeng Ma, Beijing (CN); Huishao He, Beijing (CN); Jianping Chang, Beijing (CN); Xiang Zou, Beijing (CN); Linxia Tan, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 262 days.

(21) Appl. No.: 15/271,713

(22) Filed: Sep. 21, 2016

(65) Prior Publication Data
US 2017/0138902 A1 May 18, 2017

(30) Foreign Application Priority Data

Nov. 18, 2015 (CN) .......................... 2015 1 0796142

(51) Int. Cl.
*G01N 1/02* (2006.01)
*G01N 27/62* (2006.01)
(Continued)

(52) U.S. Cl.
CPC ............ *G01N 27/622* (2013.01); *G01N 1/02* (2013.01); *G01N 1/22* (2013.01); *G01N 30/7206* (2013.01);
(Continued)

(58) Field of Classification Search
None
See application file for complete search history.

(56) References Cited

U.S. PATENT DOCUMENTS 5,109,691 A 5/1992 Corrigan et al.
5,162,652 A 11/1992 Cohen et al.
(Continued)

FOREIGN PATENT DOCUMENTS

CN 101936825 A 1/2011
CN 103293561 A 9/2013
(Continued)

OTHER PUBLICATIONS

UK Examination Report for corresponding UK Patent Application No. GB1616472.5 dated Oct. 31, 2017, 4 pages.
(Continued)

*Primary Examiner* — Peter J Macchiarolo
*Assistant Examiner* — Jermaine L Jenkins
(74) *Attorney, Agent, or Firm* — Merchant & Gould P.C.

(57) ABSTRACT

The present invention discloses darkroom type security inspection apparatus and method. An apparatus comprises a housing constituting a closed darkroom, and assemblies disposed inside the housing. The assemblies disposed inside the housing are communicated by fittings or connectors and comprises: a sampling assembly comprising a sample collecting unit and a conveyer unit configured to convey an object to be inspected into the sample collecting unit; a sample processing assembly configured to concentrate and analyze the sample; and, an inspecting assembly configured to inspect composition of the sample by means of a gas chromatographic-ion mobility spectrometer (GC-IMS) or a separated ion mobility spectrometer (IMS). The security inspection apparatus of the present invention can perform the sampling easy, rapidly and effectively and perform the inspection accurately and rapidly without destroying and unpacking an object to be inspected, and thus is suitable for requirements of on-site rapid inspection of forbidden items in the airport, customs and the likes.

11 Claims, 5 Drawing Sheets (51) Int. Cl.
*G01N 1/22* (2006.01)
*G01N 30/72* (2006.01)
(52) U.S. Cl.
CPC ....... *G01N 30/72* (2013.01); *G01N 2001/022* (2013.01); *G01N 2001/024* (2013.01)

(56) References Cited

U.S. PATENT DOCUMENTS

| | | |
|---|---|---|
| 6,895,801 B1 | 5/2005 | Fine et al. |
| 7,595,487 B2 * | 9/2009 | Fedorov ............... H01J 49/066 137/808 |
| 8,047,053 B2 * | 11/2011 | Call .................... G01N 1/2202 73/28.01 |
| 8,405,024 B2 * | 3/2013 | Li ........................ G01N 27/622 250/286 |
| 8,451,974 B2 * | 5/2013 | Morton ................. G21K 1/025 378/57 |
| 2006/0243071 A1 | 11/2006 | Sagi-Dolev |

FOREIGN PATENT DOCUMENTS

| | | |
|---|---|---|
| CN | 104517799 A | 4/2015 |
| CN | 205139052 U | 4/2016 |
| EP | 2 138 870 A3 | 6/2010 |
| WO | 2007/145616 A2 | 12/2007 |

OTHER PUBLICATIONS

Chinese Office Action for corresponding Chinese Patent Application No. 201510796142.8 dated Jul. 11, 2017, 7 pages.
Great Britain Search Report for corresponding Great Britain Patent Application No. GB1616475.8 dated Dec. 1, 2016, 6 pgs.

* cited by examiner

DARKROOM TYPE SECURITY INSPECTION APPARATUS AND METHOD

This application claims benefit of Serial No. 201510796142.8, filed 18 Nov. 2015 in China and which application is incorporated herein by reference. A claim of priority is made to the above disclosed application.

TECHNICAL FIELD

The present invention relates to the field of security inspection technology, and in particular, to darkroom type baggage security inspection apparatus and method based on an IMS and its associated technologies.

BACKGROUND

In today's society, science and technology change rapidly, economic globalization continues to develop in depth. Terrorist attacks, food safety, medical security, drug trafficking and other serious social problems threaten people's lives and property, health and safety. In order to maintain the normal social order and protect the people's life, property, health and safety, in recent years, detection technology and related equipment based on various detection principles develop rapidly.

Ion mobility spectrometry (IMS) technology, due to its characteristics of simple structure, high sensitivity, and rapid analysis, is widely used for detections and monitors in chemical warfare agents, drugs, explosives and other aspects of environmental monitoring Due to the excellent performance of IMS, a variety of equipments and technologies based on IMS technology and its related associated technologies have gradually emerged in detection fields of foods, cosmetic and pharmaceutical health. Gas chromatography-ion mobility spectrometry (GC-IMS) associated technology with full use of the separation characteristics of the GC and rapid response, high sensitivity of the IMS, not only effectively solves both low discriminative ability of the GC and cross sensitivity problem of the IMS during detection of the mixture, but also can obtain the retention time, drift time of an object to be detected in a migration passage and signal strength of the object to be detected inducted in the Faraday disc, so that obtained 3D map information of the object to be detected can be used to perform effectively an accurate recognition. In future GC-IMS detection technology will strongly apply on the fields of riot against terrorism, drug trafficking, environmental monitoring, food safety, medical supervision and health, and the like.

However, traditional IMS and its associated equipments mainly are in forms of handheld, portable, benchtop and door-type, etc. In the practical applications, they are inconvenience in sampling, resulting in low detection efficiency, or an object to be detected needs to be destroyed. And, the object to be detected such as baggage needs to unpack, which is very inconvenient.

It is desired that product using the IMS or associated technology has high sampling efficiency, high collecting speed, and high accuracy without destructive sampling, and can realize fast on-site inspection without unpacking. Moreover, it is expected that an apparatus, which has characteristics of chemical detection and strong detection capability of rapid detections on goods of various sizes, can be used in the existing customs and other occasions.

SUMMARY

In view of the above, it is an object of the present invention to provide a security inspection apparatus, which overcomes at least some abovementioned problems and can perform on-site sampling inspection accurately and rapidly without any destructions.

According to an aspect of the present invention, there is provided a darkroom type security inspection apparatus comprising a housing constituting a closed darkroom and assemblies disposed inside the housing. The assemblies disposed inside the housing comprises: a sampling assembly comprising a sample collecting unit configured to collect a sample and a conveyer unit configured to convey an object to be inspected from an outside into an expected position within the sample collecting unit; a sample processing assembly configured to concentrate and analyze the sample; and an inspecting assembly configured to inspect composition of the sample by means of a gas chromatographic-ion mobility spectrometer or a separated ion mobility spectrometer; wherein, the sampling assembly, the sample processing assembly and the inspecting assembly are communicated by fittings so that collection, processing and inspection of the sample are performed on the object to be inspected, that has been conveyed into the housing constituting the closed darkroom, within the housing.

This darkroom type baggage security inspection apparatus can provide an convenient, rapid and effective sampling and conveying method and a rapid and accurate detection means, to achieve a rapid trace detection without unpacking and destructing the items to be inspected. It is suitable for rapid inspections on drugs, explosions, prohibited volatile chemical agent, solid surface contaminations in airports, customs and the likes.

In order to achieve the above technical object of the present invention, technical solutions of the present invention can be achieved as follows: the analysis equipment can be used for fast GC-IMS, IMS, GC-IMS-MS and other apparatuses.

BRIEF DESCRIPTION OF THE DRAWINGS

In order to provide a more clear understanding of contents of the present invention, the embodiments of the present invention will be further described hereinafter in detail and completely with reference to the attached drawings, in which.

LISTS OF THE NUMBERS IN THE DRAWINGS balance strut;
housing of the security inspection apparatus;
103 conveyer belt;
104 conveyer belt brace;
**104*l* lower limb of the conveyer belt brace 104**;
**104*u* upper limb of the conveyer belt brace 104**;

105 eddy flow guiding plate;
106 eddy flow hole;
107 O-ring seal;
108 baggage to be inspected;
109 inflation passage;
110 gas guiding chamber (sampling chamber);
110I inner wall of the gas guiding chamber (sampling chamber) 110;
111 thermal sleeve;
112 inflatable pump;
113 exhaust passage;
114 exhaust pump;
115 heating filter;
116 bottom clamping net;
117 semi-permeable membrane;
118 top clamping net;
119 top tundish-shaped cover;
120 sample collecting connection passage;
121 sample collecting connection passage heating sleeve;
122 heating rod;
123 temperature sensor;
124 sample collection interface;
125 sample suction pump interface;
126 sample suction pump;
127 heat-resistance O-ring seal;
128 piston cylinder;
129 piston rod;
130 absorption sieve drum;
131 thermal insulation pad;
132 thermal desorption chamber;
133 liner passage;
134 carrier gas inlet;
135 shunting/sweeping interface;
136 MCC column;
137 thermal conductive sheath;
138 double-mode ion mobility spectrometry;
139 sample carrier gas interface;
140 infrared sensor;
141 roll-up door;
220 sample outlet.

DETAILED DESCRIPTION OF THE EMBODIMENTS

Exemplary embodiments of the present invention will be described hereinafter in detail with reference to the attached drawings, wherein the like reference numerals refer to the like elements.

Figure 1:
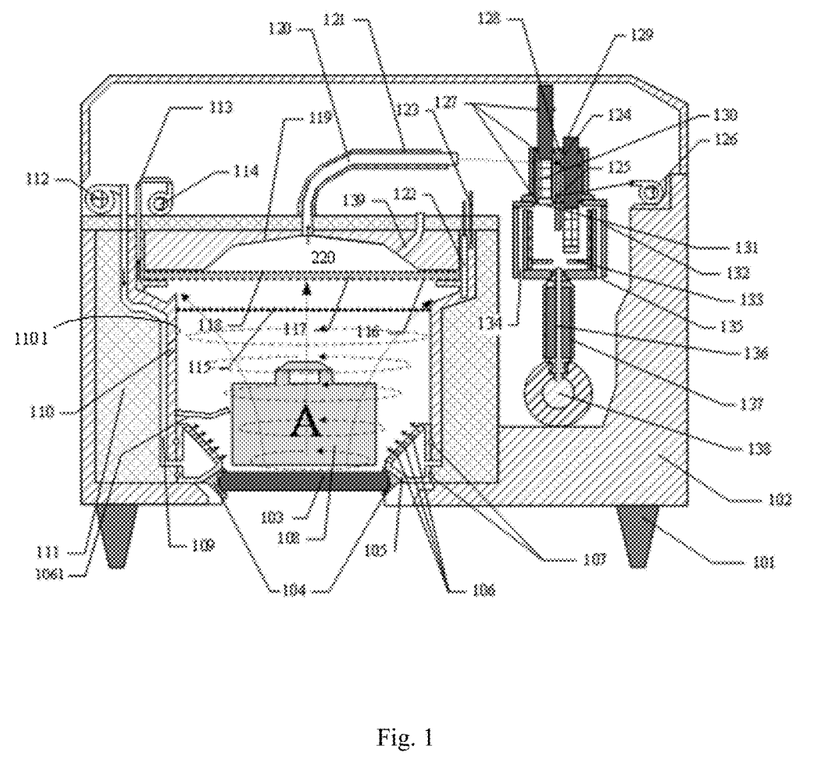
FIG. 1 is a schematic view showing a sampling process of a darkroom type baggage security inspection apparatus according to the present invention.
Figure 2:
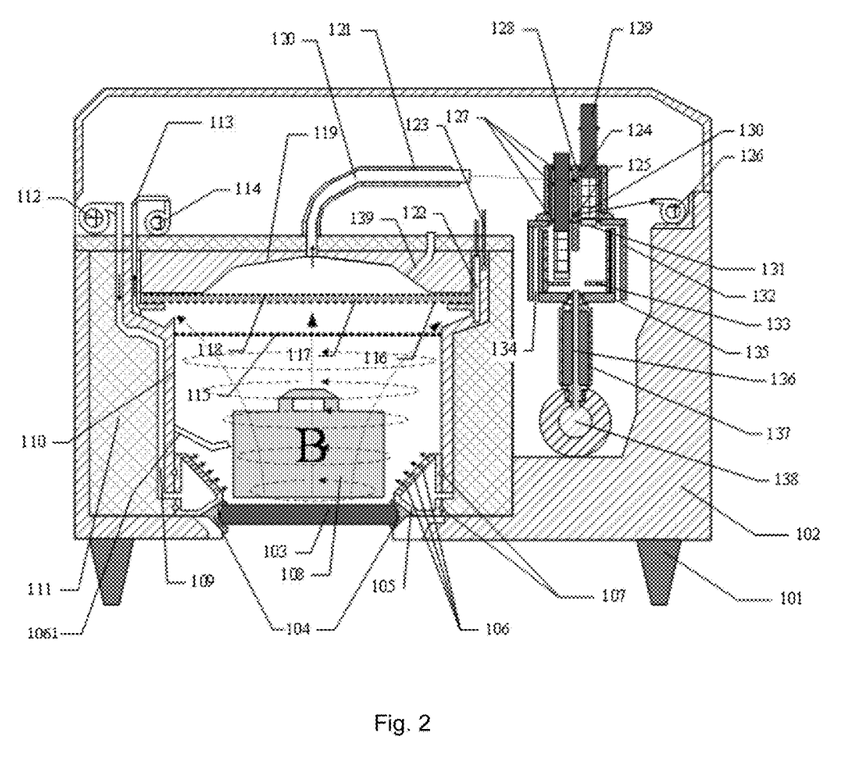
FIG. 2 is a schematic view showing a sample thermally desorbing process of a darkroom type baggage security inspection apparatus according to the present invention.
Figure 3:
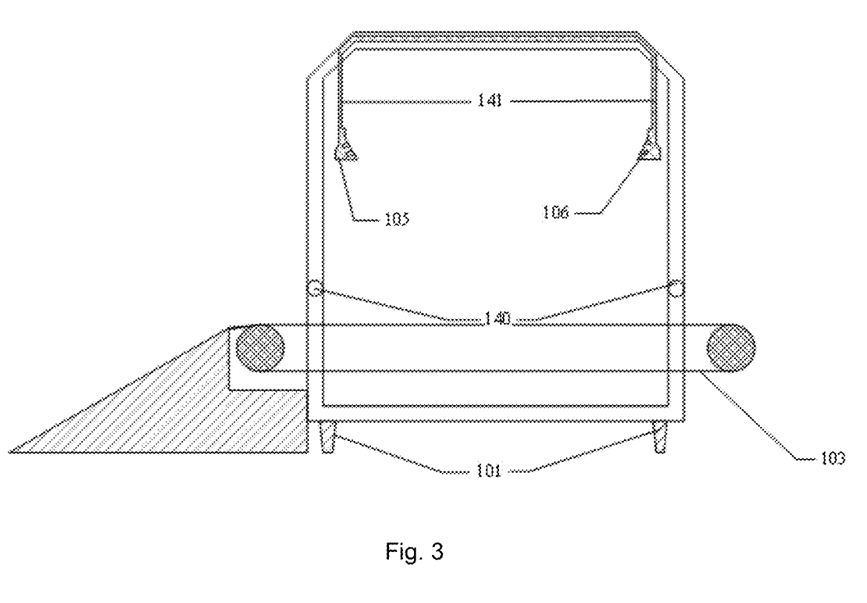
FIG. 3 is a side schematic view of a darkroom type baggage security inspection apparatus according to the present invention.

In accordance with embodiments of the present invention, a darkroom type security inspection apparatus based on an ion mobility spectrometry (IMS) and its associated technologies, for example, a darkroom type baggage rapid security inspection apparatus (as shown in FIGS. 1 and 2), is provided. The apparatus comprises a housing constituting a closed darkroom, and assemblies disposed inside the housing. The assemblies disposed inside the housing comprises a sampling assembly, a sample processing assembly, and a sample inspection assembly which are communicated by fittings for example including connection tubes or connectors.

The assemblies disposed inside the housing of the security inspection apparatus comprises a tornado type sampling chamber, a full time pre-concentration sampler, a thermal desorption chamber, a chromatographic column, a thermal insulation unit, an ion mobility spectrometry and the like. In the darkroom type baggage rapid security inspection apparatus of an embodiment of the present invention, a plurality of balance struts 101 are used to support the housing 102 and the chassis main body of the security inspection apparatus. Preferably, the balance struts comprise rubber-sleeved steel posts having elastic and flexible legs. In the darkroom type baggage rapid security inspection apparatus of an embodiment of the present invention, a conveyer belt 103 is used to convey a baggage to be inspected 108 and to support the baggage to be inspected 108, and the conveyer belt 103 is driven by a reducing motor. Conveyer belt braces 104 for being in an engagement with the conveyer belt are mounted as both sides of the conveyer belt 103 so that the conveyer belt braces 104 allow the conveyer belt 103 to move but form a seal together with the conveyer belt when the conveyer belt does not move, so as to form a sealed environment inside the whole darkroom. The conveyer belt brace 104 is made of deformable material and comprises an upper limb and a lower limb. When the conveyer belt does not move, a negative pressure is produced so that the conveyer belt braces 104 are deformed to press against the conveyer belt 103 by the upper limb and the lower limb so that external air or other substances will not enter the darkroom through between the conveyer belt 103 and the conveyer belt braces 104, reducing interference of collection, analysis and detection of the sample from external. It should be understood by those skilled in the art that other units configured to convey the sample may be provided in accordance with requirements. The conveyer belt braces 104 may be in other shapes. For example, a limb of the conveyer belt brace contacting the conveyer belt 103 may include a curved portion that may be formed of soften material liking silicone. Once a negative pressure is produced inside the sampling chamber, the curved portions are attached to edges of the conveyer belt 103 and press against the edges of the conveyer belt 103. In one embodiment of the present invention, the conveyer belt braces 104 may further comprise other deformable sheets. The deformable sheets allow the conveyer belt 103 to move, however, when a negative pressure is produced inside the sampling chamber, the sheets are attached closely to edges of the conveyer belt 103 and press against the edges of the conveyer belt 103 to form a seal. The deformable sheets are preferably made of impermeable materials, for example flexible material including rubber material and the like. In one embodiment, the sheets comprise an upper sheet and a lower sheet.

In one embodiment of the present invention, an additional nozzle 1061 for injecting hot air flow is included inside the housing of the security inspection apparatus. When being blown to an article such as a baggage to be inspected 108, the hot air flow separates or volatile the sample adhered to the baggage to be inspected 108, enhancing efficiency of collecting the sample. Moreover, the additional nozzle 1061 may be provided adjacent to the baggage to be inspected 108, achieving improved sweeping and heating effect. In addition, a direction of sweeping gas flow of the additional nozzle 1061 is closes to (instead of oppositely or inversely) a gas inflating direction of the tornado inflation port, as a result, the sweeping gas flow of the additional nozzle 1061 may accelerate formation of the tornado gas flow and thus facilitate the sample collection. In one embodiment, the additional nozzle 1061 comprises a plurality of additional nozzles 1061, of which the directions of sweeping gas flow follow to the tornado gas flow direction, as a result, the gas flow at the additional nozzles 1061 facilitate to accelerate formation of the tornado gas flow. In one embodiment, the direction of sweeping gas flow of the additional nozzle 1061 may not be the same or be close to the tornado gas inflating direction.

In other embodiments of the present invention, edges of the conveyer belt 103 are formed with grooves which are located in the middle of the edges of the conveyer belt 103 or in other locations and are extended continuously along the conveyer belt 103. The conveyer belt braces 104 comprise ribs which are able to be fitted into the grooves located in the edges of the conveyer belt 103. A seal is formed between the conveyer belt 103 and the conveyer belt braces 104 when the ribs of the conveyer belt braces 104 are fitted into the grooves located in the edges of the conveyer belt 103 under the action of negative pressure. In this embodiment, preferably, the ribs of the conveyer belt braces 104 are made of soften material or deformable material.

An infrared sensor 140 is mounted at a side wall of the housing nearing an entrance door of the security inspection apparatus. When the infrared sensor 140 senses that the baggage to be inspected 108 is completely moved into the inside of the sampling chamber of the security inspection apparatus, the reducing motor starts to reduce speed or to stop the operation, so that the conveyer belt 103 is decelerated or stopped, roll-up doors 141 provided at a conveyer belt inlet and a conveyer belt outlet of the housing are rolled down, so that a closed darkroom is formed in the whole housing.

The darkroom type security inspection apparatus of an embodiment of the present invention comprises the sampling assembly comprising a sample collecting unit and a conveyer unit configured to convey an object to be inspected into an expected position within the sample collecting unit. The sample collecting unit comprises a sampling chamber having a first end and a second end opposite to the first end, the conveyer unit is located at the first end, and the sampling chamber further comprises a sample outlet adjacent to the second end and configured to discharge the sample. The sampling chamber further comprises an inflation port 106 and a exhaust port formed at an inner wall of the sampling chamber, the inflation port 106 is configured to introduce a gas flow and the exhaust port is configured to discharge the gas, so as to produce a tornado type gas flow within the sampling chamber, and the tornado type gas flow moves spirally from the first end to the second end of the sampling chamber so that the sample carried by the object to be inspected is conveyed by the tornado type gas flow to be nearby the second end.

Figure 4:
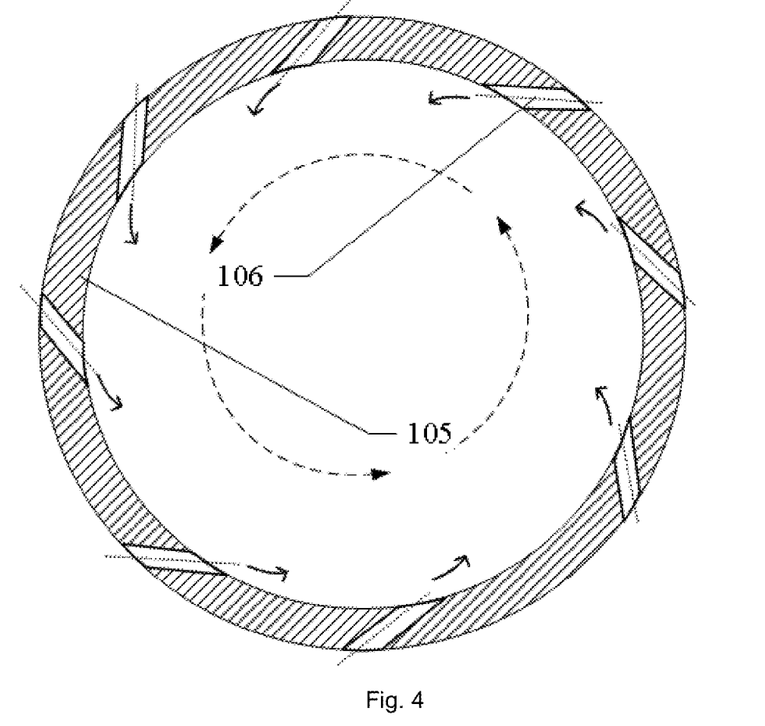
FIG. 4 is a top cross-sectional view of an eddy flow guiding plate (formed as a full circle guiding plate) of a darkroom type baggage security inspection apparatus according to the present invention.
Figure 5:
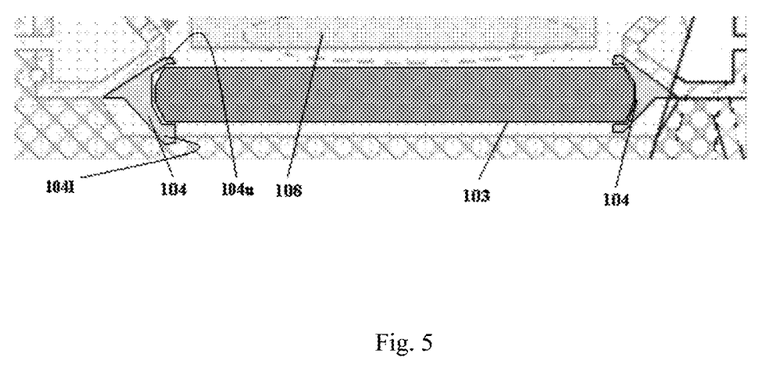
FIG. 5 is an enlarged view of a portion of the apparatus shown in FIG. 1.

Specially, the eddy flow guiding plate 105 distributed on side walls of the housing and the roll-up doors just form a whole circle, and the inflation port 106 is provided on the eddy flow guiding plate 105, as shown in FIG. 4. Inner wall of the eddy flow guiding plate 105 forms as a portion of the inner wall of the sampling chamber and has its cross section of conical shape shown in FIG. 1, that is, the inner wall of the eddy flow guiding plate 105 and the inner wall of the sampling chamber together form a frustoconical shape having a smaller-diameter round end adjacent to the chamber and a larger-diameter round end adjacent to the second end. The sampling chamber may be in other forms, for example, some more portions of the inner wall of the chamber is in a frustoconical shape having a smaller-diameter round end served as the first end and a larger-diameter round end served as the second end.

After formation of the darkroom, the inflatable pump 112 and the exhaust pump 114 go to operate. Gas is introduced by the inflatable pump into the sampling chamber through the inflation port 106 via the inflation passage 109. The inflation port is configured so that an axially inflating direction of the inflation port is mostly tangent with an inner surface of the inner wall of the chamber and is inclined towards the sample outlet side. The gas flow discharged from the eddy flow hole 106 of the eddy flow guiding plate 105 forms an eddy flow, so as to form a sampling tornado within the darkroom under the action of the inflatable pump 112, the exhaust pump 114 and the sample suction pump 126.

According to embodiments of the present invention, a heating rod 122, a thermal sleeve 111, and a gas guiding chamber 110 protected by the thermal sleeve 111 are provided at side wall of the housing of the security inspection apparatus. The gas guiding chamber may be a sampling chamber. The tornado or tornado gas flow is heated within the gas guiding chamber 110 and the inflation passage which are heated by the heating rod 122 and is thermal insulated by the thermal sleeve 111, to form a heated tornado. Strong suction action of the hot tornado suctions solid small particulate sample adhered to surface of the baggage to be inspected 108 and gaseous sample released from volatile or semi-volatile article packed in the baggage. In addition, the hot tornado helps rapid volatilization of the highly volatile or volatile prohibited items packed in the baggage, facilitating sample collection and detection. The sample suctioned by the hot tornado passes quickly through the heating filter 115 provided inside the gas guiding chamber 110 and is quickly heated by high temperature heating filter 115. The heating filter 115 on one hand prevents large particulates from entering and blocks passage, on the other hand heats the sample suctioned by the tornado, especially, heats rapidly the solid small particulate sample and volatiles some of them. The volatilized sample, together with the highly volatile sample, may pass through the semi-permeable membrane and enter the adsorber and the inspecting assembly, for analysis and detection.

Hot gas flow is discharged through an exhaust passage 113 under the action of the exhaust pump 114. The hot gas flow does not produce a convection below the heating filter 115, effectively avoiding the baggage to be inspected to be suffered from the heat. Volatilized gas from the highly volatile sample contained in the baggage to be inspected can pass directly through the bottom clamping net 116, the semi-permeable membrane 117 and the top clamping net 118 after passing through the heating filter 115 and enter a space of a top tundish-shaped cover 119. The nonvolatile solid sample volatiles some gaseous sample by the rapidly heating of the heating filter 115, and then the volatilized gaseous sample passes through the bottom clamping net 116, the semi-permeable membrane 117 and the top clamping net 118 and enters the space of the top tundish-shaped cover. Semi-permeable membranes are provided below the heating filter and the top tundish-shaped cover. The semi-permeable membrane is clamped by two metal sheets which, on one hand, are used for fixation of the semi-permeable membrane and, on the other hand, can prevent the semi-permeable membrane to be torn under the action of the strong tornado. Material for the semi-permeable membrane can selectively filter out substances to be passed through. Material for the semi-permeable membrane can prevent other contaminants including water molecules, ammonia molecules contained in the carrier gas from passing through, so as to avoid pollution of rear chromatographic column or migration passage. In addition, the semi-permeable membrane can also prevent formation of the clusters, improving resolution ratio of the apparatus. The gas guiding chamber of this design allows the apparatus to achieve samplings of volatile, semi-volatile substances and surface contaminations, broadening selectivity to the substance to be inspected.

According to embodiments of the present invention, a thermal insulation unit is provided in the sampling passage, effectively preventing condensation of the inhaled samples and even pollutions of the passage caused by the condensation.

The sample reached at the space of the top tundish-shaped cover 119 and the carrier gas coming from the sample carrier gas interface 139 are mixed in the cover with loophole and reach the pre-concentrated sample adsorber after passing through the sample collecting connection passage 120 and the sample collection interface 124. A full-time pre-concentrated sample adsorber is used to achieve a full-time collection of the sample, greatly improving detection efficiency of the apparatus.

The mixed gas containing the sample and the carrier gas is firstly conveyed to the sample processing assembly. The sample processing assembly is configured to concentrate and analyze the sample. The sample processing assembly comprises a pre-concentrated sample adsorber comprising an absorption sieve drum configured to concentrate the sample and the piston rod configured to deliver the sample in the absorption sieve drum through a piston, and a thermal desorption chamber configured to desorb the sample in the absorption sieve drum at high temperature and to mix the sample with suitable carrier gas.

The mixed gas containing the sample is conveyed to the absorption sieve drum 130 of the pre-concentrated sample adsorber and is absorbed by adsorbent in the sieve drum. The sample collecting connection passage 120 is coated with a sample collecting connection passage heating sleeve 121 heated to maintain high temperate in the passage, effectively preventing condensation of the inhaled samples and even pollutions of the passage caused by the condensation. Under the continuous action of the sample suction pump 126, enrichment and concentration of the sample in the absorption sieve drum 130 can be achieved.

After concentration of the sample, under the action of the motor, the absorption sieve drum 130 is pushed from the piston rod 129 of the piston-type adsorber to the thermal desorption chamber 132 at high temperature. Preferably, the thermal desorption chamber is manufactured of stainless steel and nickel plated copper material with stable chemical properties. Preferably, the pre-concentrated sample adsorber comprises two or more absorption sieve drums, and correspondingly, a plurality of piston rods.

The sample absorbed to the adsorber is rapidly desorbed in the thermal desorption chamber 132 at high temperature, is mixed with the pre-heated carrier gas coming from the carrier gas inlet 134, is brought to the MCC column 136 by the carried gas, and then is performed a pre-separation in the MCC column 136. After performing the pre-separation, it is guided to the double-mode ion mobility spectrometry 138, for detection and analysis. Use of the technology of double-mode ion mobility spectrometry achieves on-site detection of the positive and negative ions of substance on the same time, improving detection efficiency of the apparatus.

Preferably, the thermal insulation pads 131 provided below the piston cylinder 128 and the absorption sieve drum use materials with low thermal conductivity, such as PTFE, PEEK, which effectively isolates thermal conduction between the thermal desorption chamber 132 and the adsorber during the sample absorption process, facilitating the sample absorption.

The thermal desorption chamber 132 is provided with a carrier gas shunting/sweeping interface 135. Once it cannot be received completely by the MCC column 136, the mixed sample gas is discharged at the shunting/sweeping interface 135. In addition, the shunting/sweeping interface 135 is completely opened to perform a sweeping operation to the thermal desorption chamber 132, so as to discharge the sample and impurities in the chamber, effectively reducing appearance of ghost peaks in a twice-sampling process. Meanwhile, glass liner passage 133 with stable chemical property is hermetically embedded into the thermal desorption chamber 132. The liner passage 133 is replaceable periodically, which, on one hand, prevents the sample gas from contacting and being reacted with metal material and thereby avoiding distortions of the detected sample and the detecting signal, on the other hand, prevents large particulate matter from entering and blocking the chromatographic column.

According to embodiments of the present invention, provision of the heating filter 115 not only obtains some volatile gas by heating the sample, especially solid particulate sample, and passes the gas through the semi-permeable membrane, but also prevents large particulate impurities from entering and blocking the passage. The semi-permeable membrane 117 can effectively prevent other contaminants including water molecules, ammonia molecules contained in the carrier gas from entering, so as to avoid pollution of rear chromatographic column or migration passage. In addition, the semi-permeable membrane can also prevent formation of the clusters, improving resolution ratio of the apparatus.

According to embodiments of the present invention, during the sampling process and the desorbing process, provision of the heat-resistance O-ring seal effectively ensures a seal connection between a piston-type adsorber and a piston cylinder 128, to ensure sample collection efficiency and sample analysis efficiency. The thermal conductive sheath 137, on one hand, is used to protect the MCC 136, on the other hand, is also provided with sealed interfaces for connections between the MCC and the thermal desorption chamber 132, the double-mode ion mobility spectrometry 138. Meanwhile, it facilitates a MCC heating insulation by an external heating circuit. When the sample is pushed to the thermal desorption chamber for performing a thermal desorption, the roll-up door opens, the conveyer belt 103 operates, a baggage to be inspected (A) is conveyed out at the entrance door of the security inspection apparatus while another baggage to be inspected (B) is conveyed into the darkroom at the exit door of the security inspection apparatus. Once the baggage to be inspected is completely in the darkroom, the roll-up door closes again, and a tornado sampling assembly is formed, to begin another sampling. The operations are performed repeatedly, to achieve real-time collection and detection of a plurality of objects to be inspected.

According to embodiments of the present invention, a method of inspecting an object to be inspected using a darkroom type security inspection apparatus is described. The method mainly comprises a sample collecting process, a sample treatment process, and a sample detecting process.

First is the sample collecting process. A baggage to be inspected is placed on the conveyer belt 103 of the safety-inspection apparatus and is conveyed to the darkroom. With infrared sensing control, front and back doors of the darkroom is switched from an open state to a closed state, and the conveyer belt 103 is decelerated or stopped. Air is blown, under the action of an air pump, from eddy flow holes arranged spirally around the darkroom to the baggage to be inspected, while, a sampling suction nozzle located at the middle of the top of the darkroom and exhaust passages located at laterals of the top of the darkroom draw the air under the action of a high power air pump, in the darkroom. With a cooperation among the three, a tornado is formed. Solid small particulate sample adhered to surface of the baggage and gases released from volatile or semi-volatile article packed in the baggage passes through the heating filter and thus are heated. Some gases released from the solid small particulate sample and the volatile gaseous sample together pass through the semi-permeable membrane, and are suctioned, under the action of the sample suction pump, through the thermal insulation sampling passage and into a piston-type full-time pre-concentration and adsorption chamber, for performing a sample adsorption. Two piston-type adsorbers are used alternately to achieve full-time sample adsorption, and the sample suction pump performs a continuous gas suctioning to achieve a sample concentration.

Here are the sample treatment process and the sample detecting process. The absorption sieve drum with adsorbed and concentrated sample of the piston-type adsorber is pushed quickly into the thermal desorption chamber, the sample adsorbed to the adsorbent is instantly desorbed at high temperature, and the desorbed sample is mixed with the pre-heated chromatographic carrier gas from the bottom of the thermal desorption chamber and then is introduced to an analysis and detecting part (the MCC and the IMS) for performing the desorption of the sample.

Specifically, the darkroom type security inspection apparatus of the present invention comprises an overall chassis main body. The chassis main body comprises a conveyer belt, a housing, a gas guiding chamber, a thermal sleeve for chamber, roll-up doors located at an entrance door conveyer belt and at an exit door conveyer belt and mounted with eddy flow guiding plates aside, eddy flow guiding plate mounted at both sides of the bottom of the chassis, a conveyer belt brace 104 embedded in both sides of the conveyer belt 103, an air suction hole at the top of the chassis, an inflatable pump, an exhaust pump, an inflation passage, an exhaust passage, a heating filter, a sample collecting passage, a gas guiding chamber, a semi-permeable membrane together with its clamping elements, a top tundish-shaped cover, and the likes. The conveyer belt 103 is controlled by a variable speed motor and is used for conveying the baggage to be inspected through the darkroom. Once the baggage to be inspected is placed on the conveyer belt, the belt transfers the baggage to be inspected to the darkroom. When it is detected by the infrared sensing assembly mounted at a lateral wall of the chassis adjacent to the entrance door that the baggage to be inspected has been completely in the interior of the chassis, the reducing motor starts to reduce the speed or to stop the operation (namely, the conveyer belt 103 is decelerated or stopped), the roll-up doors at the entrance door and the exit door of the security inspection apparatus are rolled down, to form a closed darkroom in the chassis. Here, the eddy flow guiding plate 105 distributed on side walls of the chassis and the eddy flow guiding plates located at the roll-up doors adjacent to the entrance door and the exit door just form a whole circle, and, a plurality of loops of the eddy flow holes arranged in a spiral form on the eddy flow guiding plate are also formed. The inflatable pump, the exhaust pump and the sample suction pump start to operate, and air from the inflatable pump passes though the passages within the housing of the chassis and is discharged at eddy flow holes arranged in a spiral form of the bottom of the chassis, to form a spiral air flow. The formed spiral air flow is pulled up by the exhaust pump and the sample suction pump at the top of the chassis, to form a strong tornado. Under the action of strong suction action of the tornado, solid small particulate sample adhered to surface of the baggage and trace gas released from volatile or semi-volatile article packed in the baggage are passed through the heating filter at the upper portion of the gas guiding chamber. Gaseous sample of volatile article is passed through the semi-permeable membrane directly under the action of the tornado gas flow, and then is introduced through the thermal insulation sample collecting passage to the adsorber, for performing a sample adsorption and collection. The solid small particulate sample adhered to surface of the baggage, which is suctioned by the tornado, is firstly heated rapidly between the heating filter and the semi-permeable membrane to release some gaseous sample, then, the released gaseous sample is passed through the semi-permeable membrane, and is introduced through the thermal insulation sample collecting passage to the adsorber, while, the solid particulate residues are discharged by the exhaust pump, preventing them from polluting the passages or adversely affecting detection of next baggage to be inspected. Both the inflatable pump and the exhaust pump are used to provide continuous circulating winds for generation of the tornado. Power of the inflatable pump may be chosen in accordance with requirements. Since gas amplification action of the tornado, flow velocity of the exhaust pump is 10 times or more than the inflatable pump, so that a negative pressure is formed to facilitate adsorption of the sample. In order to avoid the air flow from the inflatable pump disturb the sample suctioned from the sampling target, on one hand, the air source for the air flow from the inflatable pump is required to be away from the sampling target as far as possible, for example, a flexible soft tube is adopted to apart the pump from the sampling port, on the other hand, the air flow from the inflatable pump is filtered and purified, to avoid cross contamination among the gases, improving sensitivity of the sampling operation of the apparatus. The gas guiding chamber can be heated. The thermal sleeve for chamber is used for thermal insulations of the whole gas guiding chamber as well as the inflation passage between the gas guiding chamber and the thermal sleeve. Generally, temperature in the gas guiding chamber or in the darkroom may be set to be higher 10-20 degrees Celsius than room temperature, on one hand, achieving the safety, on the other hand, promoting rapid volatilization of highly volatile or volatile prohibited items packed in the baggage, thereby facilitating the sample collection. Conveyer belt braces 104 are provided specially at both sides of the conveyer belt 103. Dense bristles are adopted in a portion of the brace 104 contacting the conveyer belt 103. The brace 104 as well as its bristles ensures that the darkroom is sealed in an optimal manner when performing a tornado sampling process, preventing the detection from being adversely affected due to a large amount of air flow from the bottom of the belt. The semi-permeable membrane is clamped by two metal sheets which, on one hand, are used for fixation of the semi-permeable membrane and, on the other hand, can prevent the semi-permeable membrane to be torn under the action of the strong tornado. Material for the semi-permeable membrane can prevent other contaminants including water molecules, ammonia molecules contained in the carrier gas from passing through, so as to avoid pollution of chromatographic column or migration passage. In addition, the semi-permeable membrane can also prevent formation of the clusters, improving resolution ratio of the apparatus.

According to one embodiment of the present invention, the sample collecting connection passage is made of metal, chemically stable fluorine rubber or Teflon passage. Wall of the passage is provided with heating film and insulation cotton. During the entire sample collection process, the sample collecting connection passage is maintained at high temperature (100~250 degrees Celsius), which effectively eliminates sample loss or passage contamination caused by sample condensation to inner wall of the passage.

According to one embodiment of the present invention, the full time pre-concentration sampler mainly includes a double piston cylinder, a piston-type absorber, and a heat-resistance O-ring seal for the sealing between the piston cylinder and piston-type adsorber. Preferably, the double piston cylinder is manufactured by PTFE or PEEK materials with good thermal insulation properties, good mechanical properties and stable chemical properties. The heat-resistance O-ring seal is used for the sealing between the piston cylinder and piston-type adsorber. The absorber piston mainly consists of a piston rod body in an upper part of the adsorber, an adsorber sieve drum in the middle part of the adsorber and a thermal insulation pad located in the bottom part of the adsorber. Preferably, the piston rod is made of PTFE and is driven by the motor. During the sample collection and sample analysis, the electrode can drive the piston-type absorber to be movable hermetically between the piston cylinder and the thermal desorption chamber. The adsorber sieve drum, preferably, is made of chemically stable inert metal, and adsorbent can be placed inside the hollow sieve drum. Diameter of the adsorbent materials should be greater than diameter of outer wall of the sieve drum passage. The adsorbent material can be added according to demands of user's main detection target. The thermal insulation pad, preferably, is made of PTFE material with good thermal insulation properties and stable chemical properties. The thermal insulation pad can effectively isolate thermal exchange between the thermal desorption chamber and the absorption sieve drum, facilitating adsorption and concentration of the sample. The thermal insulation pad and the absorption sieve drum are connected by screws, which facilitates replacements of the thermal insulation pad and of adsorbent materials. During a detecting process, two piston-type adsorbers are used alternately to achieve full-time sample adsorption, improving detection efficiency of the apparatus.

According to one embodiment of the present invention, the thermal desorption chamber is coated with a heating film for heating the chamber. Meanwhile, insulation cotton is coated outside the heating film for thermal insulation of the chamber. A temperature sensor is further installed on the chamber and is for real-time monitoring and controlling temperature inside the chamber through an external temperature control circuit. Temperature programmed mode is used in the thermal desorption chamber as well as the abovementioned passage heating assembly, which can effectively reduce the power consumption. During the sampling desorbing process, one piston-type adsorber with adsorbed and concentrated sample is pushed quickly under the driving of the motor into the thermal desorption chamber at high temperature, at the same time, another piston-type adsorber with desorbed and detected sample is pulled out under the driving of the motor and waits for adsorption and concentration of sample of next baggage to be inspected. The sample adsorbed to the piston-type adsorber which is pushed into the thermal desorption chamber is instantly desorbed and then is mixed with the carrier gas from bottom of the thermal desorption chamber, after that, it is introduced to a chromatographic column for performing a pre-separation, finally, it is introduced to the IMS for performing a detection.

According to one embodiment of the present invention, the use of porous capillary columns (MCC) with small volume, high column efficiency and rapid separation speed can overcome problems existing in conventional capillary column, including long time (10~15 minutes) analysis, requirements on large volume furnace for high temperature demand, to meet requirements on the rapid on-site detection.

According to one embodiment of the present invention, the temperature-control assembly comprises a heating system, a temperature control system, a thermal insulation unit, temperature sensor and a temperature control circuit. This assembly is mainly used for the heating, heat insulation and temperature control of the sample collecting connection passage, the gas guiding chamber, the heating filter, the thermal desorption chamber, the chromatographic column and the ion migration passage. Preferably, the sample collecting pipe thermal, the desorption and the migration passage are heated by the heating film, the gas guiding chamber is heated by a heating rod or a heating blanket, and the heating net is heated by heating wires with fast heating property. Preferably, the thermal insulation unit uses insulation cottons, which are mainly used together with the temperature-control assembly, for thermal insulations of these temperature-control devices, on the one hand, reducing temperature difference between different locations or parts and improving accuracy of the detection, on the other side, reducing the overall energy consumption.

According to one embodiment of the present invention, the ion mobility spectrometry is in a positive and negative double-mode. The positive and negative double-mode ion mobility spectrometry can achieve on-site detections on positive and negative ions from the baggage to be inspected at the same time. Compared with the single mode, it needs no switching on electric field, shortens the detection time, and improves the detection efficiency. In addition, the migration passage is made of high temperature resistant ceramic materials, greatly broadening the range of the samples to be detected.

The apparatus of the present invention has the following advantages.

The apparatus uses a closed tornado sampling assembly which is capable of performing a full sampling on a baggage to be inspected. Meanwhile, because the tornado sampling way has strong suctioning force, it can greatly improve collection efficiency on volatile or semi-volatile samples in the baggage or solid particulate sample adhered to surface of the baggage, to achieve a direct sampling on volatile or semi-volatile matters in the baggage or surface contamination solid matters without unpacking the baggage.

This darkroom type baggage security inspection apparatus can perform a concentration on the collected sample during detection of the sample, reduce the detection limit of requirements of IMS detector, reduce difficulty of development of the apparatus and cost of the apparatus, realize the positive and negative ion detection at the same time to establish a correlation between positive and negative maps, and improves the detection speed compared with a single mode. This darkroom type baggage security inspection apparatus adopts full-time pre-concentrated sample collection technology, which can greatly enhance the sampling efficiency and improve detection efficiency of the apparatus.

Compared with routine X-ray based baggage security inspection apparatus, this darkroom type baggage security inspection apparatus has improved detection sensitivity on volatile or semi-volatile prohibited items carried in baggage, can accurately inform of prohibited items without unpacking, and can also eliminate the disadvantages of conventional X-ray based baggage security inspection apparatus, namely, it mainly depends on subjective judgment, to make up for defects of X-ray security inspection apparatus in relevant fields.

Although several exemplary embodiments of the present invention have been shown and described, it would be appreciated by those skilled in the art that various changes or modifications may be made in these embodiments without departing from the principles and spirit of the present invention, the scope of which is defined in the claims and their equivalents.

What is claimed is:

1. A darkroom type security inspection apparatus comprising: a housing constituting a closed darkroom, and assemblies disposed inside the housing, wherein the assemblies disposed inside the housing comprise:
    a sampling assembly comprising a sample collecting unit configured to collect a sample and a conveyer unit configured to convey an object to be inspected from an outside into an expected position within the sample collecting unit;
    a sample processing assembly configured to concentrate and desorb the sample; and
    an inspecting assembly configured to inspect composition of the sample by means of a gas chromatographic-ion mobility spectrometer or a separated ion mobility spectrometer;
    wherein, the sampling assembly, the sample processing assembly and the inspecting assembly are communicated by fittings so that collection, processing and inspection of the sample are performed on the object to be inspected, that has been conveyed into the housing constituting the closed darkroom, within the housing.

2. The darkroom type security inspection apparatus according to claim 1, wherein, the conveyer unit of the sampling assembly comprises a conveyer belt and a conveyer belt brace, edges of both sides of the conveyer belt and the conveyer belt brace are configured to match each other so that the conveyer belt brace allows the conveyer belt to move but forms a seal together with the conveyer belt when the conveyer belt does not move.

3. The darkroom type security inspection apparatus according to claim 2, wherein, the conveyer belt brace is made of deformable material and comprises an upper limb and a lower limb; and, when the conveyer belt does not move, a negative pressure is produced within the housing constituting the closed darkroom so that the conveyer belt brace is deformed to press against the conveyer belt by the upper limb and the lower limb so as to form the seal.

4. The darkroom type security inspection apparatus according to claim 1, wherein, the sample collecting unit comprises a sampling chamber having a first end and a second end opposite to the first end, the conveyer unit is located at the first end, and the sampling chamber further comprises a sample outlet adjacent to the second end and configured to discharge the sample;
    the sampling chamber further comprises an inflation port and an exhaust port formed at an inner wall of the sampling chamber, the inflation port is configured to introduce a gas flow and the exhaust port is configured to discharge the gas, so as to produce a tornado type gas flow within the sampling chamber, and the tornado type gas flow move spirally from the first end to the second end of the sampling chamber so that the sample carried by the object to be inspected is conveyed by the tornado type gas flow to be nearby the second end.

5. The darkroom type security inspection apparatus according to claim 4, wherein, the inflation port is configured so that an axially inflating direction of the inflation port is substantially tangent with an inner surface of the inner wall of the chamber and is inclined towards the sample outlet side.

6. The darkroom type security inspection apparatus according to claim 4, wherein, the inner wall of at least a part of the sampling chamber is formed in a frustoconical shape having a smaller-diameter round end adjacent to the chamber and a larger-diameter round end adjacent to the second end.

7. The darkroom type security inspection apparatus according to claim 1, wherein, the sampling assembly comprises a heating filter configured to filter the sample when the sample is conveyed from the first end to the second end, and to heat the sample so as to facilitate volatilization of the sample carried by the object to be inspected.

8. The darkroom type security inspection apparatus according to claim 1, wherein, the sampling assembly comprises a semi-permeable membrane configured to selectively filter the sample, and the semi-permeable membrane is disposed within the sampling chamber to compart a space for mixing with carrier gas.

9. The darkroom type security inspection apparatus according to claim 1, wherein, the sample processing assembly comprises a pre-concentrated sample adsorber comprising an absorption sieve drum configured to concentrate the sample and a piston rod configured to deliver the sample in the absorption sieve drum through a piston; and
    a thermal desorption chamber configured to desorb the sample in the absorption sieve drum at high temperature and to mix the sample with suitable carrier gas.

10. The darkroom type security inspection apparatus according to claim 1, wherein, the inspecting assembly comprises porous capillary columns configured to pre-separate the sample, and an ion mobility spectrometry.

11. A method of inspecting an object to be inspected using a darkroom type security inspection apparatus, the method comprising:
    placing the object to be inspected on the conveyer unit, and conveying the object to be inspected into the darkroom type security inspection apparatus via the conveyer unit; and
    implementing an inspection on the object to be inspected using the darkroom type security inspection apparatus according to claim 1.

* * * * *